United States Patent
Graban et al.

(10) Patent No.: US 10,543,158 B2
(45) Date of Patent: *Jan. 28, 2020

(54) AUTOPHAGY ACTIVATING COMPLEX, COMPOSITIONS AND METHODS

(71) Applicant: W Skincare, LLC, Boca Raton, FL (US)

(72) Inventors: Suzanne E. Graban, Boca Raton, FL (US); Richard C. Wang, Dallas, TX (US); Konstantinos M. Lahanas, Ramsey, NJ (US)

(73) Assignee: W SKINCARE, LLC, Boca Raton, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/489,328

(22) Filed: Apr. 17, 2017

(65) Prior Publication Data

US 2018/0296462 A1 Oct. 18, 2018

(51) Int. Cl.

| | |
|---|---|
| *A61K 8/60* | (2006.01) |
| *A61Q 19/08* | (2006.01) |
| *A61K 8/49* | (2006.01) |
| *A61Q 19/00* | (2006.01) |
| *A61Q 19/02* | (2006.01) |
| *A61Q 17/04* | (2006.01) |

(52) U.S. Cl.
CPC .............. *A61K 8/60* (2013.01); *A61K 8/4953* (2013.01); *A61Q 19/08* (2013.01); *A61K 2800/884* (2013.01); *A61Q 17/04* (2013.01); *A61Q 19/007* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 4,996,317 A * | 2/1991 | O'Brien | ............ A23F 5/206 210/511 |
| 5,989,557 A | 11/1999 | Bombardelli | |
| 7,700,084 B2 | 4/2010 | Delage-Grouiller | |
| 7,763,289 B2 | 7/2010 | Bommarito | |
| 7,776,915 B2 | 8/2010 | Morarin | |
| 8,101,211 B2 | 1/2012 | Chiba | |
| 8,512,764 B2 | 8/2013 | Paufique | |
| 8,568,749 B2 | 10/2013 | Sanmiguel | |
| 8,828,458 B2 | 9/2014 | Morariu | |
| 9,050,255 B2 | 6/2015 | Vilinsky | |
| 9,138,400 B2 | 9/2015 | Paufique | |
| 9,238,000 B2 | 1/2016 | Khusial | |
| 9,289,374 B2 | 3/2016 | Chevreau | |
| 2004/0081714 A1 | 4/2004 | Pauly | |
| 2007/0134193 A1 | 6/2007 | Pauly et al. | |
| 2007/0292543 A1 | 12/2007 | Schnee | |
| 2009/0324705 A1 | 12/2009 | Vikhrieva | |
| 2011/0207681 A1 | 8/2011 | Klein | |
| 2011/0306568 A1 | 12/2011 | Schwarz | |
| 2015/0190339 A1 | 7/2015 | Khusial et al. | |
| 2015/0297592 A1 | 10/2015 | Bilstein | |
| 2015/0342854 A1 | 12/2015 | Shibuya | |
| 2016/0101029 A1 | 4/2016 | Serrano Sanmiguel | |

FOREIGN PATENT DOCUMENTS

WO WO-2011006938 A1 * 1/2011 ............. A61K 31/02

OTHER PUBLICATIONS

Cuervo, A., Autophagy and Aging, Trends Genet, Dec. 2008, pp. 604-612, vol. 24, issue 12, retrieved from https://www.ncbi.nlm.nih.gov/pmc/articles/PMC2745226/, retrieved on Feb. 23, 2017, 12 pages.

PCT/US18/27950, PCT Notification of Transmittal of the International Search Report and the Written Opinion of the International Searching Authority, or the Declaration, International Filing Date Apr. 17, 2018, dated Jul. 13, 2018, received by mail Jul. 17, 2018, 26 pages.

Azevedo, et al., Extraction of Caffeine, Chlorogenic Acids and Lipids from Green Coffee Beans using Supercritical Carbon Dioxide and Co-Solvents, Brazilian Journal of Chemical Engineering, vol. 25, No. 03, pp. 543-552, Jul.-Sep. 2008, 10 pages.

Remenapp, et al. Efficacy of an Autophagy-Activitating Skincare Regiman in the Treatment of Photoagingskin, Journal of Complementary Medicine & Alternative Healthcare, vol. 1 issue 5, Mar. 2017, 4 pages.

Technical Datasheet Myramaze ®, RAHN AG, Zurich, Dorflisrassse, Oct. 10. 2017. pp. 1-7.

* cited by examiner

*Primary Examiner* — David J Blanchard
*Assistant Examiner* — Sarah J Chickos
(74) *Attorney, Agent, or Firm* — Brian S. Steinberger; Hilary F. Steinberger; Law Offices of Brian S. Steinberger, P.A.

(57) ABSTRACT

Compositions, methods, and processes are used in topical applications for human or animal skin. A combination of five (5) active ingredients: caffeine, trehalose, asparagus extract, ceramide 2 (2%) and a resurrection plant, *Myrothamnus flabellifolia*, extract are used in a topical formulation, such as a cream, lotion, spray or gel to boost or activate autophagy, the body's innate processes for repairing cell damage. The five active ingredients are combined in different formulations to provide at least six (6) products for topical application, including, but not limited to, a cleanser, a spray essence, a day cream, a night cream, a serum and a booster. The five (5) active ingredients provide a unique biological composition, hereinafter called, "autophagy activating complex," that changes the way skin ages, restores and renews radiance.

17 Claims, 5 Drawing Sheets

FIGURE 1

STEP ONE - 10
Select Ingredients
Trehalose: Caffeine: Regu-scence (asparagus plant extract): Ceramide 2 (2%) solution: Myramaze (resurrection plant extract):

STEP TWO - 20
Weigh 200 mg of caffeine

STEP THREE - 30
Weigh 200 mg of trehalose

STEP FOUR - 40
Weigh 600 mg of Reguscence (~550 µl)

STEP FIVE - 50
Mix caffeine, trehalose, and Reguscence in 18.2 mL ddH₂O, heat the mixture to 37°C and agitate by vortexing to ensure complete solubilization.

STEP SIX - 60
Generate a 25% solution in DMSO by adding 1 g of Ceramide into 4 mL DMSO. This solution must agitated extensively by vortexing.

STEP SEVEN -70
Agitate the 25% Ceramide stock solution while simultaneously adding 800 µl into the ddH₂O containing caffeine, trehalose, and Reguscence. Heat the solution to 37°C and agitate by vortexing.

STEP EIGHT -80
Add 1 mL of Myramaze stock solution to the solution containing caffeine, trehalose, Reguscence, and ceramide. Heat the solution to 37°C and agitate extensively.

STEP NINE - 90
Recover 10x solution containing

| | |
|---|---|
| Caffeine | 1% |
| Trehalose | 1% |
| Reguscence | 6% |
| Ceramide | 1% |
| Myramaze | 5% |

FIGURE 2

DAY TIME- 250

| 255 -Step 1 | Cleanser – use first thing in the morning |
|---|---|
| 260 -Step 2 | Serum – apply to freshly cleansed skin |
| 265 -Step 3 | Day Cream – apply over serum, prior to any makeup |
| 270 -Step 4 | Essence – mist several times throughout day (can be applied over other products and/or makeup) |

NIGHT TIME - 350

| 355 -Step 1 | Cleanser – use in the evening, prior to bed |
|---|---|
| 360 -Step 2 | Serum – apply to freshly cleansed skin |
| 365 -Step 3 | Night Cream – apply over serum, prior to bed |

| Ingredient | Cocktail % (w/w) |
|---|---|
| Caffeine | 0.1 |
| Trehalose | 0.1 |
| Reguscence | 0.6 |
| Ceramide 2 (2%) | 0.1 |
| Myramaze | 0.5 |

Western Blot Analysis of Compound

AUTOPHAGY ACTIVATING COMPLEX, COMPOSITIONS AND METHODS

This invention relates to methods, processes and compositions for topical application to the skin which comprises a novel combination of five core components in a cosmetically acceptable vehicle; the use of such compositions provide benefits to the skin, boosts autophagy activity within skin cells, improves the skin condition, changes the way skin ages, restores and renews radiance to animal or human skin.

BACKGROUND AND PRIOR ART

Human skin is the outer covering of the body and is the largest organ of the body. Human skin performs monumental functions twenty-four hours a day, seven days a week from birth to death.

A basic discussion of the various functions of the skin is found on the Internet website, https://en.wikipedia.org/wiki/Human_skin. On this website it teaches that the skin performs the function of protection by providing an anatomical barrier from pathogens and damage between the internal and external environment in bodily defense. The skin contains a variety of nerve endings that react to heat and cold, touch, pressure, vibration, and tissue injury functioning to provide sensation.

The skin helps the body with heat regulation. Dilated blood vessels in the skin increase perfusion and heat loss, while constricted vessels greatly reduce cutaneous blood flow and conserve heat. Further, the skin provides a relatively dry and semi-impermeable barrier that controls evaporation or fluid loss. The skin communicates to others your mood, attractiveness, or physical state; it acts as a storage center for lipids and water, and synthesizes vitamin D by action of ultraviolet light on certain parts of the skin.

Additional functions of the skin include excretion; sweat contains urea in a much lower concentration than urine, however, by sweating it is a secondary function in temperature regulation. The skin provides a means for absorption; medicine can be administered through the skin, by ointments or an adhesive patch and has become an important site of transport to internal organs. The skin is also water resistant and acts as a water-resistant barrier so essential nutrients are not washed out of the body.

As skin ages, it becomes thinner and more easily damaged. Intensifying the effect of aging is the decreasing ability of skin to heal itself as a person ages. In addition, skin aging is accompanied by a decrease in volume and elasticity.

Attention to aging skin has been a priority for over 3000 years and the history of skin care is chronicled and summarized on the Internet website: www.glamourdaze.com/2015/02/a-short-history-of-skincare-cosmetics.html. On this website, it is reported that in ancient times, masks were used to cleanse and maintain the skin's moisture. The Egyptians used anti-wrinkle creams made with essential oil of frankincense.

In the last 2000 years, additional anti-aging skin care concoctions included scrubs, eggs, crocodile dung, muds, herbs, salves, soap, castile soap for the wealthy, toners, scented waters, acid peels, salons for facial treatments, foundations, pressed powders, moisturizers, toners, cleansers, creams with vitamin E, petrolatum, beta-hydroxy, collagen, alpha-hydroxyl acids, vitamins A, C, E and B, and in this twenty-first century, hyaluronic acid moisturizers, antioxidants, sunscreens are in the market.

The main change in cosmetic skin products has been the switch away from using animal and synthetic derived ingredients to using all or partial natural and organic ingredients. Hormonal and steroidal creams have been replaced with botanical stem cell extracts to cleanse, tone, moisturize, "plump-up" the skin to erase wrinkles, fine lines, and the like.

In 2016, the global skin care market was estimated to be worth 121 billion U.S. dollars, according to *The Statistics Portal*, www.statista.com/statistics/254612/global-skin-care-market-size. "The U.S. skin care and toiletries market in general is benefiting from rising demand for natural and organic products . . . . Companies continue to offer consumers innovative products, concentrating on developing environmentally friendly products either made locally or using locally sourced ingredients. Anti-aging products also represent a strong growth area in the U.S. market."

There are patents and patent publications that represent the state of the art for anti-aging formulations. As the patents and patent publications demonstrate, many substances are applied topically to the skin of humans in order to improve appearance, retain moisture levels, repair damage from the environment and slow down the aging process, and create a cosmetic improvement of the skin surface.

There has been a recent shift in focus from the use of topical applications to improve visual appearance of the skin surface to the use of topical applications to influence cell behavior and the effects of cell behavior on aging and disease. The cell behavior of interest is autophagy. The term autophagy means "self-eating," and refers to the processes by which your body cleans out debris, including toxins, and recycles damaged cell components.

As explained in layman's terms by Greatist at www.greatist.com (Feb. 29, 2016) "Your cells create membranes that hunt out scraps of dead, diseased, or worn-out cells; gobble them up; strip 'em for parts; and use the resulting molecules for energy or to make new cell parts."

In *Autophagy and aging; keeping that old broom working* by Ana Maria Cuervo, published online: https://www.ncbi.nlm.nih.gov/pmc/articles/PMC2745226/Nov. 5, 2008, Cuervo provides a review of evidence in support of the connections between autophagy, health span and aging.

In addition, the state of the art for anti-aging formulations using the body's autophagy process include plants or yeasts as active ingredients in cosmetic compositions.

Thus, after 3000 years, the global cosmetics industry is still actively pursuing products useful in reducing signs of aging or reducing signs of aged skin, mankind's most vital organ. Men and women are looking for new ways to stall the passage of time and improve the overall appearance of skin which is inclined to develop wrinkles, fine lines, discoloration, dullness, sagging, loss of tone, loss of elasticity, thinning, dryness and rough texture. There have been hundreds of choices in the type of skin care treatments and products available. Yet, there remains a need for cosmetic compositions which reduce the manifestations of skin aging associated with reduced autophagy activity within skin cells. The present invention meets the need for such cosmetic compositions.

SUMMARY OF THE INVENTION

A primary embodiment of this invention is to provide new compositions, methods, and processes for increasing, maintaining and/or restoring autophagy activity levels within skin cells.

A secondary embodiment of this invention is to provide new compositions, methods, and processes to improve overall appearance of skin, including treating, reversing, and/or preventing signs of skin aging or damage, such as wrinkles, fine lines, discoloration, loss of tone, loss of elasticity, thinning and the like, by activating autophagy within skin cells.

A third embodiment of this invention is to provide new compositions, methods and processes to boost autophagy activity in the skin wherein the compositions are provided in a variety of forms suitable for topical application, such as cosmetics, lotions, creams, serums, sprays, skin lotions, and cleansers.

A fourth embodiment of this invention is to provide new compositions, methods and processes to boost autophagy activity in the skin wherein the compositions are provided in a kit comprising a cleanser, a spray essence, a lotion, a serum and an anti-aging night cream.

A fifth embodiment of this invention is to provide an autophagy activating complex that helps remove toxins at the cellular level.

A sixth embodiment of this invention is to provide an autophagy activating complex that helps boost skin's integrity to prevent cellular damage.

A seventh embodiment of this invention is to provide an autophagy activating complex that helps repair cellular damage.

An eighth embodiment of this invention is to provide an autophagy activating complex that helps rebuild and repair the skin's structural network.

A ninth embodiment of this invention is to provide an autophagy activating complex that helps boost cellular energy and reinvigorate skin cell function.

A tenth embodiment of this invention is to provide an autophagy activating complex that helps repair, remove and/or recycle damaged cellular components for healthier functioning cells.

The present invention uses a combination of five (5) active ingredients: caffeine, trehalose, asparagus extract, ceramide 2 (2%) and a resurrection plant, *Myrothamnus flabellifolia*, extract in a topical formulation, such as a cleanser, serum, cream, lotion, spray or gel to boost autography, the body's innate processes for repairing cell damage. The five active ingredients are combined in different formulations to provide at least six (6) products for topical application, including, but not limited to, a cleanser, a spray essence, a day cream, a night cream, a serum and a booster. The five (5) active ingredients provide a unique biological composition, hereinafter called, "autography activating complex," that changes the way skin ages, restores and renews radiance.

Advantages of this invention include harnessing the human body's innate process for detoxifying cells and repairing cell damage, providing a more permanent and lasting improvement to the appearance of skin by addressing aging at the source from inside the body.

Further objects and advantages of this invention will be apparent from the following preferred embodiments.

BRIEF DESCRIPTION OF FIGURES

FIG. 1 is a flow chart of a process for preparing a 10× solution of the autography activating complex of the present invention.

FIG. 2 is a flow chart of a method for using the autography boosting complex in formulation of the present invention.

DESCRIPTION OF THE PREFERRED EMBODIMENTS

Figure 3:
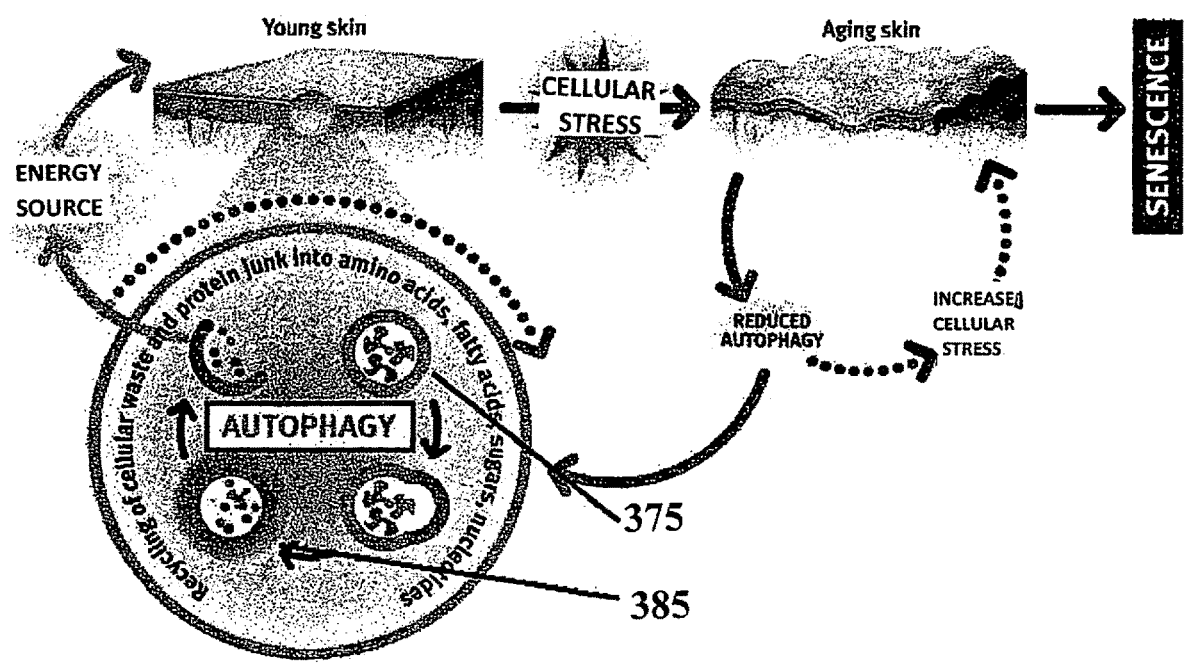
FIG. 3 is a graphic illustration of autophagy activity in skin cells showing the key markers of autophagy that were identified during in vitro experiments.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

The following terms and acronyms used in the Detailed Description are defined below.

The term "approximately" can be +/−10% of the amount referenced.

Additionally, preferred amounts and ranges can include the amounts and ranges referenced without the prefix of being approximately.

The phrase, "autophagy activating complex" used herein, refers to a novel combination of five ingredients that include: caffeine, trehalose, asparagus extract, ceramide 2 (2%) and a resurrection plant, *Myrothamnus flabellifolia*, extract in a topical formulation.

The "asparagus extract" ingredient in the autophagy activating complex is *Navarra Asparagus officinalis* "Grolim" (D. O. Navarra Spain) the active ingredient in a commercial product marketed as Regu®-Scence with the generic label, "*asparagus officinalis* stem extract in propanediol, glycerin and water." *Navarra Asparagus* contains high quantities of saponins, known to be positive modulators of autophagy and activates autophagy, in part, due to the presence of plant saponins, a mild type of plant detergent, which has been shown to induce autophagy in vitro. Regu®-Scence is a registered trademark owned by DSM Nutritional Products, LLC, 45 Waterview Boulevard, Parsippany, N.J. 07054.

The "caffeine" ingredient in the autophagy activating complex is green caffeine extracted uniquely with carbon dioxide ($CO_2$) for the purest and most potent caffeine extract for activating autophagy. $CO_2$ is forced through the green coffee beans which are then sprayed with water at high pressure to remove the caffeine. The caffeine is then isolated for resale by passing the water through activated charcoal filters or by distillation, crystallization or reverse osmosis.

The "Ceramide-2" ingredient in the autography activating complex is a type of sphingolipid known to influence autophagy and play a key role in barrier repair and hydration. Ceramides, components of cellular membranes were shown to affect cellular self-destruction such as apoptosis and autophagy. It activates autophagy through several independent pathways: the inhibition of Akt (through PP2A), activation of Beclin, inhibition of nutrient uptake, and promotion of autophagosome-lysosome fusion. Some evidence links ceramides to effect on a membrane protein that acts as nutrient transporters and activates autophagy induced starvation. Other topical benefits of ceramides are water-retention capacity, in addition to, barrier repair and cell regulation. The extracellular matrix of the skin is composed of 50% ceramides.

The "resurrection plant" extract used in the autophagy activating complex is from the specific resurrection plant *Myrothamnus flabellifolia*, in an extract commercially available under the trademark, MYRAMAZE. *Myrothamnus flabellifolius* is a plant species in the genus *Myrothamnus* found in Southern Africa. It is also called the resurrection plant, for the speed with which apparently dead leaves revive when the rains come. *Myrothamnus flabellifolius* is a natural autography activator; it protects membrane structures from dehydration and skin lipids against oxidative stress. The MYRAMAZE trademark is owned by RAHN AG Corporation Switzerland, Zurich, Switzerland.

The "trehalose" ingredient used in the autophagy activating complex is a plant sugar associated with the upregulation of autophagy. Trehalose is known to moisturize and protect the skin and activates autophagy in an mTOR independent manner. Other topical benefits are rehydrating and water binding properties that allow the skin to retain moisture.

The phrase, "cosmetically acceptable delivery vehicle" is used herein to describe the components of the formulation other than the active ingredients of the autophagy activating complex that are generally recognized as safe and nontoxic at the levels employed to achieve 100% weight of the formulation applied or delivered to the skin surface.

The signs of aging, both visible and invisible, are a result of cellular damage. The autophagy activating complex ingredients of the present invention harnesses the body's autophagy, the biological process of cellular repair and renewal by which toxins and damaged components of cells are removed, repaired or recycled for new, healthier cells.

Autophagy not only has a significant impact on age-related diseases, it can help explain why we wrinkle, get dark spots and duller skin. As we age, our autophagy naturally becomes less efficient. Waste builds up in cells, which are unable to detoxify and repair as they once were, leading to the visible signs of aging.

In FIG. 1, a process for making a 10× solution of the autography activating complex of the present invention is provided. The individual ingredients and process for mixing are identified. In Step one 10, the individual ingredients: trehalose, caffeine, asparagus plant extract, ceramide2 (2%) and resurrection plant extract are selected. Step two 20, 200 milligrams (mg) of caffeine in the form of a white to off-white crystalline powder is weighed. Step three 30, 200 mg of trehalose, a white crystalline powder is weighed. Step four 40, 600 mg or approximately 550 microliters (μl) of an asparagus plant extract is weighed. The asparagus plant extract is commercially available under the trademark, REGU-SCENCE, a transparent to slightly turbid liquid that is dark yellow to pale brown in appearance.

In Step five 50, the weighed portions of caffeine, trehalose, and asparagus plant extract is mixed in 18.2 ml of double distilled water (ddH$_2$O) to form a solution. The solution is heated to 37° C. and agitated by vortexing to ensure complete solubilization. The resulting solution is clear and colorless.

In Step six 60, a 25% stock solution of Ceramide 2 is prepared in dimethylsulfoxide (DMSO) by adding 1 gram of Ceramide into 4 ml DMSO. This solution is also agitated by vortexing forming a cloudy colorless mixture.

In Step seven 70, the 25% stock solution of Ceramide 2 is agitated while simultaneously adding 800 μl into the ddH$_2$O solution containing caffeine, trehalose, asparagus plant extract; then heated to 37° C. and agitated by vortexing. The resulting Ceramide 2-ddH$_2$O solution containing caffeine, trehalose, asparagus plant extract is slightly cloudy and colorless.

In Step eight 80, 1 ml of a resurrection plant (commercially available under the trademark MYRAMAZE, a red brown liquid) is added to the Ceramide 2-ddH$_2$O solution containing caffeine, trehalose, asparagus plant extract; then heated to 37° C. and agitated by vortexing.

In Step nine 90, a slightly cloudy and lightly tan colored solution is recovered that has a 10× strength composed of 1% caffeine, 1% trehalose, 6% asparagus plant extract, 1% Ceramide 2 and 5% resurrection plant extract. This 10× solution can be frozen into aliquots of 1 ml and stored at −80° C. It must be heated to 37° C. for thirty minutes and agitated by vortexing when thawed from frozen.

The unique autophagy activating complex of the present invention is found in every formula. The complex contains five skin beneficial ingredients that work synergistically across three key cellular pathways to boost autophagy in vitro.

The Table below provides the ingredients in the autophagy activating complex together with the weight percent used in the formulations developed.

TABLE OF INGREDIENTS AND FORMULATIONS FOR AUTOPHAGY ACTIVATING COMPLEX

| Ingredient | Cleanser % (w/w) | Essence % (w/w) | Day Cream % (w/w) | Night Cream % (w/w) | Serum % (w/w) | Booster % (w/w) |
|---|---|---|---|---|---|---|
| Caffeine | 0.05 | 0.25 | 0.5 | 0.5 | 0.5 | 0.50 |
| Trehalose | 0.05 | 0.25 | 0.25 | 0.25 | 0.25 | 0.50 |
| REGU ® SCENCE Asparagus plant extract | 0.30 | 0.1 | 3.00 | 3.00 | 3.00 | 3.00 |

-continued

TABLE OF INGREDIENTS AND FORMULATIONS FOR
AUTOPHAGY ACTIVATING COMPLEX

| Ingredient | Cleanser % (w/w) | Essence % (w/w) | Day Cream % (w/w) | Night Cream % (w/w) | Serum % (w/w) | Booster % (w/w) |
|---|---|---|---|---|---|---|
| Ceramide 2 (2%) | 0.05 | 0.001 | 1.00 | 1.00 | 1.00 | 2.00 |
| MYRAMAZE ® Resurrection plant extract | 0.25 | 0.1 | 0.1 | 0.1 | 0.1 | 0.50 |
| Total % (w/w) | 0.7 | 0.70 | 4.85 | 4.85 | 4.85 | 6.50 |

The autophagy activating complex of the present invention can be formulated in a variety of forms for topical application and comprise active ingredients, as shown in the Table above, from about 0.7% to approximately 6.5% by weight of the total composition that includes a cosmetically acceptable vehicle in an amount needed to complete the total 100% weight of the product for topical delivery of each formulation.

A cosmetically acceptable vehicle may take the form of any known in the art that is suitable for application to skin. The vehicle may comprise an aqueous phase, an oil phase, an alcohol, a silicone phase or mixtures thereof. The cosmetically acceptable vehicle may also comprise an emulsion. Non-limiting examples of suitable cosmetically acceptable vehicles are disclosed in U.S. Pat. No. 9,238,000, entitled, "Method of Improving Aging Appearance of Skin by Modulation of WIPI-1"; the teachings are incorporated herein by reference.

In the present invention, compositions comprising a cosmetically or dermatologically acceptable formulation include the novel autophagy activating complex and are suitable for contact with living animal tissue, including human tissue, with virtually no adverse physiological effect to the user.

Suitable cosmetic product forms for the compositions of this invention are shown in the examples below.

Example 1: Cleanser

The cleanser is formulated to gently exfoliate dead skin cells, dissolve pore-clogging impurities, soothe and condition and prepare skin for the rest of regimen.

A 125 milliliter (ml)/4.7 fluid ounce batch of a anti-aging cleanser is prepared by first mixing an autophagy activating complex with the following weight ratios:

| Ingredient | % (w/w) Range |
|---|---|
| Caffeine | 0.03-0.07 |
| Trehalose | 0.03-0.07 |
| Asparagus plant extract | 0.20-0.40 |
| Ceramide 2 (2%) | 0.01-0.20 |
| Resurrection plant extract | 0.05-0.35 |

The remaining percentage of the composition to achieve 100% weight comprises approximately 99.68% (w/w) to approximately 98.91% (w/w) of a cosmetically acceptable vehicle, such as, oil/water emulsion to achieve a rich, creamy cleanser that gently exfoliates skin to enhance cellular renewal and promotes clarity. The delivery vehicle can also include pomegranate extract to gently remove excess oil and dulling impurities to re-texturize skin and tighten appearance of pores and Tsubaki oil and rosehip oil to reduce inflammation and replenish essential lipids for improved texture and a comfortable after feel. The skin is left conditioned, comfortable and primed for the rest of the regimen.

Example 2: Essence

The essence product is formulated to protect the skin from harmful environmental stressors, rehydrate, energize, soothe and condition the skin.

A 75 milliliter (ml)/2.5 ounce batch of a hydrating essence spray is prepared by first mixing an autophagy activating complex with the following weight ratios:

| Ingredient | % (w/w) Range |
|---|---|
| Caffeine | 0.15-0.35 |
| Trehalose | 0.15-0.35 |
| Asparagus plant extract | 0.05-0.5 |
| Ceramide 2 (2%) | 0.0001-0.01 |
| Resurrection plant extract | 0.05-0.20 |

The remaining percentage of the composition to achieve 100% weight comprises approximately 98.6% (w/w) to approximately 96.9% (w/w) of a cosmetically acceptable vehicle, such as, water formation containing 83% green tea extract to achieve a pH-balancing mist that shields the skin from environmental pollutants and aggressors while sealing in hydration and soothing skin. Additional ingredients included in the delivery vehicle can include orange peel oil to help detoxify skin, while high potency antioxidants including polyphenols, white tea, vitamin B and vitamin C offer all day protection from free radicals. In addition, nourishing fruit extracts and hyaluronic acid can be added to the delivery vehicle to revive dehydrated and dull skin, reduce puffiness and discourage the formation of wrinkles.

Example 3: Serum

The serum product is formulated to promote cellular regeneration, improve firmness and elasticity, reduce discolorations, brighten complexion, enhance skin tone and texture.

A 30 milliliter (ml)/1.0 ounce batch of a correcting serum is prepared by first mixing an autophagy activating complex with the following weight ratios:

| Ingredient | % (w/w) Range |
|---|---|
| Caffeine | 0.25-0.75 |
| Trehalose | 0.15-0.35 |
| Asparagus plant extract | 2.00-4.00 |
| Ceramide 2 (2%) | 0.50-2.00 |
| Resurrection plant extract | 0.05-1.00 |

The remaining percentage of the composition to achieve 100% weight comprises approximately 97.05% (w/w) to approximately 91.9% (w/w) of a cosmetically acceptable delivery vehicle, such as, an oil/water emulsion to achieve a serum that gives back to the skin what it naturally loses over time, the ability to self-repair. The delivery vehicle can also include probiotics and Vitamin D3 to encourage skin renewal and support collagen and elastin production, enhancing firmness and elasticity. Licorice root, niacinamide and Vitamin C can be included in the delivery vehicle to reduce dark spots and brighten skin tone for a noticeably glowing complexion. The lightweight formula and ingredients adapt to the skin's unique needs and reignite luminosity, elasticity and suppleness.

Example 4: Day Cream

The day cream is formulated to include a UVA and UVB broad spectrum SPF 30 ingredient, reduce redness and inflammation, prevent collagen breakdown from damaging free radicals, provide all-day hydration and plump the skin.

A 50 milliliter (ml)/1.7 ounce batch of a day cream+SPF 30 is prepared by first mixing an autophagy activating complex with the following weight ratios:

| Ingredient | % (w/w) Range |
|---|---|
| Caffeine | 0.25-0.75 |
| Trehalose | 0.15-0.35 |
| Asparagus plant extract | 2.00-4.00 |
| Ceramide 2 (2%) | 0.50-2.00 |
| Resurrection plant extract | 0.05-1.00 |

The remaining percentage of the composition to achieve 100% weight comprises approximately 97.05% (w/w) to approximately 91.9% (w/w) of a cosmetically acceptable delivery vehicle, such as, an oil/water emulsion to achieve a day cream that delivers a precise balance of hydration and protection to actively combat the visible signs of aging. The light-weight formula plus broad spectrum SPF 30 defends against harmful ultraviolet (UV) rays and free radicals while fighting wrinkles and visibly plumping skin. Thus, also included in the delivery vehicle are the UVA and UVB broad spectrum SPF 30 ingredient, and antioxidants to protect from the sun's damaging rays and neutralize free radicals, peptides and plant stem cells to improve collagen production to visibly lift sagging skin and prevent the onset of wrinkles. Hyaluronic acid and tremella mushroom can also be added to the delivery vehicle to deeply hydrate for smooth, plump skin.

Example 5: Night Cream

The night cream is formulated to deeply moisturize and balance natural oils, lift, firm and sculpt facial contours, reduce depth of fine lines and wrinkles and revitalize dull, tired skin.

A 50 milliliter (ml)/1.7 ounce batch of a night cream is prepared by first mixing an autophagy activating complex with the following weight ratios:

| Ingredient | % (w/w) Range |
|---|---|
| Caffeine | 0.25-0.75 |
| Trehalose | 0.15-0.35 |
| Asparagus plant extract | 2.00-4.00 |
| Ceramide 2 (2%) | 0.50-2.00 |
| Resurrection plant extract | 0.05-1.00 |

The remaining percentage of the composition to achieve 100% weight comprises approximately 97.05% (w/w) to approximately 91.9% (w/w) of a cosmetically acceptable delivery vehicle, such as, a light oil/water emulsion to achieve a night cream that provides the skin with unique support needed to maximize repair and renewal during sleep. The delivery vehicle includes argan oil, Vitamin B5 and hyaluronic acid to hydrate, nourish and combat dry, dull skin and improve barrier function. Peptides along with Vitamins A and C can be included in the delivery vehicle to encourage collagen and elastin production improving firmness and diminishing the appearance of fine lines and wrinkles for smooth, plump skin. The rich, whipped texture deeply nourishes skin and redefines facial contours overnight to produce a firm and glowing complexion when waking.

Example 6: Booster

A booster product is formulated to help effectively up-regulate the skin autophagy for dramatically younger-acting skin from within.

A 30 milliliter (ml)/1.0 ounce batch of a booster cream is prepared by first mixing an autophagy activating complex with the following weight ratios:

| Ingredient | % (w/w) Range |
|---|---|
| Caffeine | 0.25-1.00 |
| Trehalose | 0.25-1.00 |
| Asparagus plant extract | 2.00-4.00 |
| Ceramide 2 (2%) | 1.00-3.00 |
| Resurrection plant extract | 0.05-1.00 |

The remaining percentage of the composition to achieve 100% weight comprises approximately 96.45% (w/w) to approximately 90.0% (w/w) of a cosmetically acceptable delivery vehicle, such as, a water based/gel-like formula to achieve a light serum that enhances skin's ability to renew itself and targets and treats visible lines while increasing skin elasticity. The delivery vehicle can include Vitamins C, D and B3 to target and treat visible lines while increasing skin elasticity.

Example 7: Autophagy Activating Complex Kit

To provide synergistic anti-aging results for the consumer of the autophagy boost complex compositions, the compositions are packaged in a kit comprising a cleanser, a spray essence, a day cream, a serum and a night cream. Since autophagy declines with age, the natural autophagy process of the skin needs continual support for skin to look its most radiant, youthful best. The products of the present invention provide around the clock support for autophagy activation with ingredients tailored to increase effectiveness in the morning, at night, and throughout the skincare regimen For example, during the day, skin should be protected from the damaging environmental factors such as UV rays and free radicals which not only contribute to the visible signs of aging, they can damage cellular components and hinder autophagy. In addition to the autophagy activating complex, the day cream provides SPF and antioxidant support to ward off environmental damage. On the contrary, night is the optimal time to maximize skin's natural renewal process and restore moisture lost throughout the day. Therefore, in addition to the autophagy activating complex, the night cream contains essential oils and vitamins to replenish moisture and improve the skin's natural barrier. While, all of the products contain the autophagy activating complex, they each include supplementary ingredients that provide skin an additional range of anti-aging benefits and will yield the greatest results when used as a system.

FIG. 2 is a flow chat of how the products of this invention are used by a consumer. A day time procedure 250 includes using the cleanser on the face, neck and arms to cleanse the skin in the morning 255, then applying the serum to the freshly cleansed skin 260. A day cream is then applied over the serum 265, prior to any makeup or other cosmetics. A spray essence is applied over the cleanser, serum and day cream 270; this essence is in the form of a mist and can be used several times throughout the day and over other cosmetic products including make-up.

FIG. 2 also shows a night time procedure 350 that includes cleansing the skin with a cleanser in the evening 355, prior to bed; followed by the application of a serum to the freshly cleansed skin 360. The next step is the application of a night cream over the serum 365. The night cream maximizes repair and renewal of skin cells during sleep.

In vitro testing of the autophagy activating complex is reported below. FIG. 3 is a graphic illustration of autophagy activity in skin cells providing an overview of the autophagy cycle. The key markers identified during the in vitro experiments were the conversion of LC3 protein 375 and the detection of autophagosomes by fluorescence 385. The presence of these two markers provided evidence that the recycling of cellular waste and protein junk into amino acids, fatty acids, sugars, and nucleotides was occurring, creating energy for cellular repair and renewal.

Figures 4A, 4B:
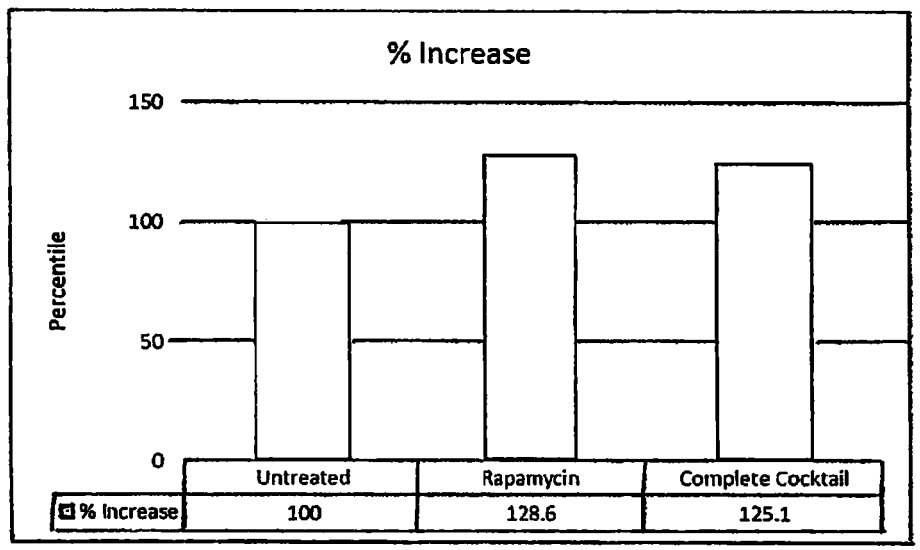
FIG. 4A shows the formulation used in in vitro experiments conducted to measure autophagy activity in skin cells.
FIG. 4B is a bar graph showing 25.1% increase in autophagy activity over untreated neonatal foreskin cells.

FIG. 4A shows the weight percent of each ingredient in the autophagy activating complex used in the in vitro experiments: caffeine 0.1%, trehalose 0.1%, asparagus plant extract 0.6%, ceramide 2 (2%) 0.1% and resurrection plant extract 0.5%. Thus the autophagy activating complex comprised 1.4% of the total weight of the topical application for the skin cell experiments, the remaining 98.6% of the formulation consisting of a cosmetically acceptable water-based formulation and the like.

FIG. 4B shows the autophagy activating complex of the present invention caused a 25.1% increase in autophagy activity over untreated cells. The cells were derived from neonatal foreskin.

Figure 5:
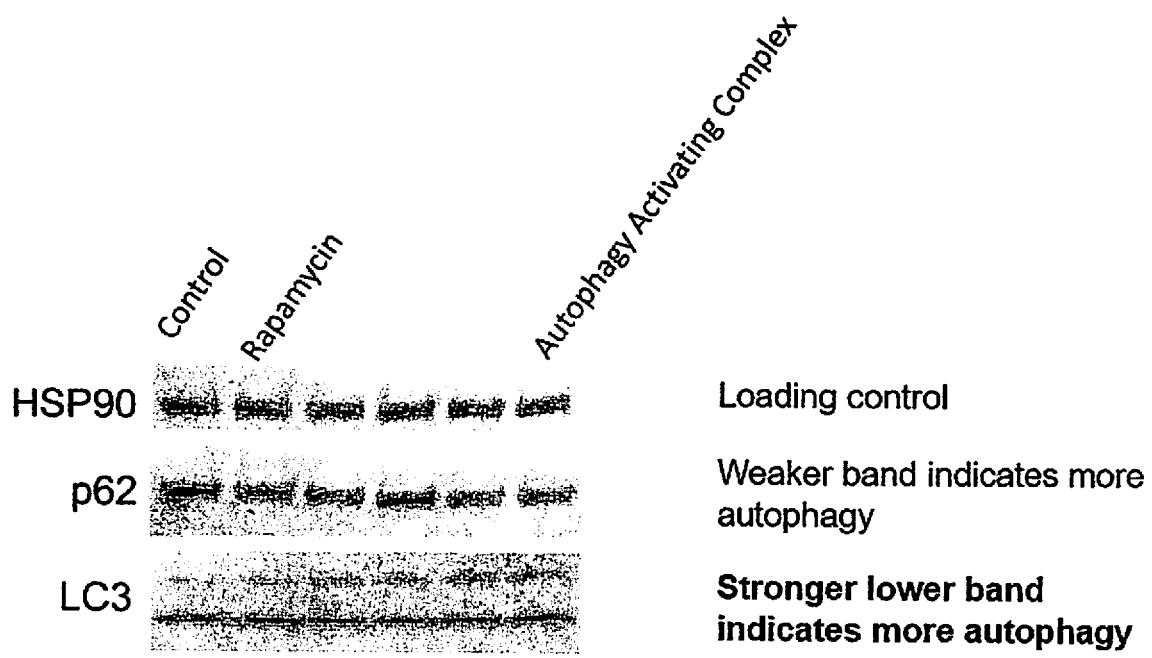
FIG. 5 shows the Western Blot analysis of the autophagy activating complex of the present invention.

FIG. 5 shows the Western Blot analysis of the autophagy activating complex of the present invention. The Western Blot is an analytical technique used in molecular biology disciplines to detect specific proteins in a sample of tissue. The p62 protein recognizes toxic cellular waste, which is then scavenged by a sequestration process known as self-eating or autophagy. Lack of autophagy leads to accumulation of p62, which is not good, as it induces a cellular stress response that leads to disease, aging and the like.

In FIG. 5, bands for p62 protein, a substrate of autophagy and LC3 a protein marker of autophagosome are identified in the blot analysis. Labeling of p62 serves as a useful marker for the induction of autophagy, clearance of protein aggregates, and the inhibition of autophagy. Labeling of LC3 serves to track the binding of p62 and subsequent recruitment of autophagosomes. When analyzing the effect of the autophagy activating complex in the Western Blot analysis, the weaker band for p62 protein indicates more autophagy; the stronger lower band for LC3 indicates more autophagy which are desired results.

In summary, the present invention provides novel, personal anti-aging skin care formulations that reduce the manifestation of skin aging associated with reduced autophagy activity within skin cells by demonstrably activating the cells internal ability to detoxify, self-repair, and recycle damaged cellular components for healthier, cells with optimal functionality.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A topical application for human or animal skin that increases the autophagy activity levels of skin cells, the topical application is a composition comprising:
   a plurality of active ingredients for increasing the autophagy activity level of the skin cells, in which the plurality of the active ingredients solely consist of effective amounts of caffeine, trehalose, asparagus plant extract, ceramide 2 and a resurrection plant extract from *Myrothamnus flabellifolius*; and
   a cosmetically acceptable delivery vehicle.

2. The topical application of claim 1, wherein the autophagy activating mixture comprises from approximately 0.7% by weight to approximately 6.5% by weight of the total composition.

3. The topical application of claim 1, wherein the cosmetically acceptable delivery vehicle comprises from approximately 93.0% by weight to approximately 99.45% by weight of the total composition.

4. The topical application of claim 2, wherein the autophagy activating mixture that comprises approximately 0.7% by weight of the composition is a formulation for a skin cleanser to exfoliate dead skin cells and prepare the skin for further treatment.

5. The topical application of claim 2, wherein the autophagy activating mixture that comprises approximately 0.70% by weight of the composition is a formulation for an essence that is sprayed on the skin to protect from harmful environmental stressors, rehydrate, energize, soothe and condition.

6. The topical application of claim 2, wherein the autophagy activating mixture that comprises approximately 4.85% by weight of the composition is a formulation for a serum to promote cellular regeneration, improve firmness and elasticity.

7. The topical application of claim 2, wherein the autophagy activating mixture that comprises approximately 4.85% by weight of the composition is a formulation for a day cream that reduces redness and inflammation, prevents collagen breakdown and provides all-day hydration.

8. The topical application of claim 2, wherein the autophagy activating mixture that comprises approximately 4.85% by weight of the composition is a formulation for a night cream that deeply moisturizes and balances natural oils, lifts, firms and sculpts facial contours, reduces depth of fine lines and wrinkles.

9. The topical application of claim 2, wherein the autophagy activating mixture that comprises approximately 6.50% by weight of the composition is the formulation for a booster that up-regulates skin autophagy for youthful skin from within.

10. The topical application of claim 3, wherein the cosmetically acceptable delivery vehicle is at least one of a water based formulation, an oil and water based emulsion, or an oil based formulation.

11. An autophagy activating complex composition for increasing, maintaining and restoring autophagy activity levels within human skin cells comprising:
 a plurality of active ingredients for increasing the autophagy activity level of the skin cells, in which the plurality of the active ingredients solely consist of:
 approximately 0.03 to approximately 1.00% by weight of caffeine;
 approximately 0.03 to approximately 1.00% by weight of trehalose;
 approximately 0.05 to approximately 4.00% by weight of asparagus plant extract;
 approximately 0.001 to approximately 3.00% by weight of ceramide 2;
 approximately 0.05 to approximately 1.00% by weight of a resurrection plant extract from *Myrothamnus flabellifolius*; and
 a cosmetically acceptable vehicle for delivery of the autophagy activating complex to the skin of a human body.

12. The autophagy activating complex composition of claim 11, wherein the caffeine is extracted from green coffee beans by a carbon dioxide extraction process.

13. The autophagy activating complex composition of claim 11, wherein the asparagus plant extract is *asparagus officinalis* stem extract in propanediol, glycerin and water.

14. The autophagy activating complex composition of claim 11, wherein the resurrection plant extract is *Myrothamnus flabellifolius* leaf/stem extract in propanediol and water.

15. The autophagy activating complex composition of claim 11, wherein the cosmetically acceptable vehicle for delivery of the autophagy activating complex to the skin is selected from at least one of a lotion, spray, cream, serum, emulsion, gel, oil, mask, essence, toner and paste.

16. A topical application for human or animal skin that increases the autophagy activity levels of skin cells, the topical application is a serum composition comprising:
 approximately 4.85% by weight of the serum composition is an autophagy activating mixture of active ingredients for increasing the autophagy activity levels of the skin cells, the active ingredients solely consist of caffeine, trehalose, asparagus plant extract, ceramide 2 and a resurrection plant extract from *Myrothamnus flabellifolius*; and
 approximately 95.15% by weight of the serum composition is a cosmetically acceptable delivery vehicle.

17. The topical application for human or animal skin of claim 16, wherein the cosmetically acceptable delivery vehicle is selected from at least one of a lotion, spray, cream, serum, emulsion, gel, oil, mask, essence, toner and paste.

* * * * *